(12) United States Patent
Morita et al.

(10) Patent No.: US 11,154,257 B2
(45) Date of Patent: Oct. 26, 2021

(54) IMAGING CONTROL DEVICE, IMAGING CONTROL METHOD, AND IMAGING CONTROL PROGRAM

(71) Applicant: FUJIFILM CORPORATION, Tokyo (JP)

(72) Inventors: Junya Morita, Kanagawa (JP); Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 329 days.

(21) Appl. No.: 16/423,169

(22) Filed: May 28, 2019

(65) Prior Publication Data
US 2019/0388051 A1   Dec. 26, 2019

(30) Foreign Application Priority Data

Jun. 25, 2018   (JP) .............................. JP2018-120295

(51) Int. Cl.
*A61B 6/02* (2006.01)
*A61B 6/00* (2006.01)
*G06T 7/00* (2017.01)

(52) U.S. Cl.
CPC .............. *A61B 6/025* (2013.01); *A61B 6/502* (2013.01); *G06T 7/0012* (2013.01);
(Continued)

(58) Field of Classification Search
CPC ....... A61B 6/025; A61B 6/502; A61B 6/4452; G06T 7/02; G06T 2207/10112
See application file for complete search history.

(56) References Cited

U.S. PATENT DOCUMENTS

| 2010/0119116 A1 | 5/2010 | Nishimura et al. |
| 2011/0075793 A1 | 3/2011 | Akahori et al. |
| (Continued) | | |

FOREIGN PATENT DOCUMENTS

| JP | H02-302248 A | 12/1990 |
| JP | 2005-137472 A | 6/2005 |
| (Continued) | | |

OTHER PUBLICATIONS

Ren Baorui et al: "Automatic patient motion detection in digital breast tomosynthesis", Medical Imaging 2011: Physics of Medical Imaging, Proc. of SPIE vol. 7961, No. 1, Mar. 3, 2011, pp. 1-12, XP060008381.

(Continued)

*Primary Examiner* — Boniface N Nganga
(74) *Attorney, Agent, or Firm* — Solaris Intellectual Property Group, PLLC

(57) ABSTRACT

An image acquisition unit acquires a plurality of projection images, which are generated by causing an imaging apparatus to perform tomosynthesis imaging for irradiating a subject with radiation under a first imaging condition for tomosynthesis imaging and which respectively correspond to a plurality of radiation source positions at the time of tomosynthesis imaging. A body movement determination unit determines whether or not the body movement of the subject is occurring during tomosynthesis imaging on the basis of the plurality of projection images. A condition setting unit sets a second imaging condition for simple imaging in the imaging apparatus in a case where the body movement is occurring.

17 Claims, 8 Drawing Sheets

(52) U.S. Cl.
CPC ............. *A61B 6/4452* (2013.01); *A61B 6/541* (2013.01); *G06T 2207/10112* (2013.01)

(56) References Cited

U.S. PATENT DOCUMENTS

| | | |
|---|---|---|
| 2012/0033868 A1 | 2/2012 | Ren et al. |
| 2017/0086770 A1* | 3/2017 | Morita ................... A61B 6/025 |
| 2017/0231593 A1 | 8/2017 | Fukuda et al. |

FOREIGN PATENT DOCUMENTS

| | | |
|---|---|---|
| JP | 2010-179094 A | 8/2010 |
| JP | 2015-188604 A | 11/2015 |
| JP | 2017-143943 A | 8/2017 |

OTHER PUBLICATIONS

Extended European Search Report dated Aug. 8, 2019, issued in corresponding EP Patent Application No. 19177105.4.

English language translation of the following: Office action dated Aug. 10, 2021, from the JPO in a Japanese patent application No. 2018-120295 corresponding to the instant patent application.

\* cited by examiner

| THICKNESS OF BREAST [mm] | SIMPLE IMAGING | | | TOMOSYNTHESIS IMAGING | | | LUT1 |
|---|---|---|---|---|---|---|---|
| | T/F | TUBE VOLTAGE [kV] | GRID | T/F | TUBE VOLTAGE [kV] | GRID | |
| 0 TO 20 | W/Rh | 26 | IN | W/Al | 26 | OUT | |
| 20 TO 30 | W/Rh | 27 | IN | W/Al | 28 | OUT | |
| 30 TO 40 | W/Rh | 28 | IN | W/Al | 30 | OUT | |
| 40 TO 50 | W/Rh | 29 | IN | W/Al | 32 | OUT | |
| 50 TO 60 | W/Rh | 30 | IN | W/Al | 34 | OUT | |
| 60 TO 70 | W/Rh | 31 | IN | W/Al | 36 | OUT | |
| 70 TO 80 | W/Rh | 32 | IN | W/Al | 38 | OUT | |
| 80 TO | W/Rh | 33 | IN | W/Al | 40 | OUT | |

…

IMAGING CONTROL DEVICE, IMAGING CONTROL METHOD, AND IMAGING CONTROL PROGRAM

CROSS REFERENCE TO RELATED APPLICATIONS

The present application claims priority under 35 U.S.C. § 119 to Japanese Patent Application No. 2018-120295 filed on Jun. 25, 2018. The above application is hereby expressly incorporated by reference, in its entirety, into the present application.

BACKGROUND

Technical Field of the Invention

The present disclosure relates to an imaging control device, an imaging control method, and an imaging control program for generating a tomographic image from a plurality of projection images by imaging a subject at each of a plurality of radiation source positions so as to acquire the plurality of projection images.

Related Art

In recent years, in a radiation image capturing apparatus using radiation such as X-rays, gamma rays and the like, in order to observe an affected part in more detail, tomosynthesis imaging has been proposed. In the tomosynthesis imaging, imaging is performed by moving a radiation source and irradiating a subject with radiation from a plurality of radiation source positions, and thereby a tomographic image, in which a desired tomographic plane is emphasized, is generated from a plurality of acquired projection images. In the tomosynthesis imaging, in accordance with the characteristics of the imaging apparatus and the necessary tomographic image, the radiation source is moved in parallel with the radiation detector or moved so as to draw a circular or elliptic arc, a plurality of projection images are acquired by imaging the subject at a plurality of radiation source positions, and the projection images are reconstructed by using a back projection method such as a simple back projection method or a filtered back projection method, whereby a tomographic image is generated. By generating such tomographic images on a plurality of tomographic planes of the subject, it is possible to separate a structure in which the tomographic planes overlap each other in the depth direction. Therefore, it is possible to find a lesion which is unlikely to be detected in a two-dimensional image acquired by conventional simple imaging. The simple imaging is an imaging method in which a subject is irradiated with radiation once to acquire one two-dimensional image which is a transmission image of the subject.

On the other hand, in the tomosynthesis imaging, there is also a problem in that the reconstructed tomographic image is blurred due to the mechanical error of the imaging apparatus and the influence of the body movement of the subject and the like caused by the time difference of imaging at each of the plurality of radiation source positions. In a case where the tomographic image is blurred as described above, particularly in a case where the breast is a subject, it is difficult to find a lesion such as minute calcification, which is useful for early detection of breast cancer. For this reason, in a case where tomosynthesis imaging is performed, the simple imaging is also performed, and thereby both a tomographic image and a two-dimensional image are generally acquired.

Further, as in the tomosynthesis imaging, in the imaging method of imaging the subject a plurality of times, a method of determining whether or not it is necessary to perform re-imaging in accordance with the magnitude of the body movement has been proposed (refer to JP2005-137472A).

On the other hand, in the situation of imaging in which body movement occurs, there is a high possibility that body movement will occur again even in a case where re-imaging is performed. For example, in a case where imaging is performed with the position of the subject tilted with respect to the horizontal direction, body movement tends to occur in the direction in which gravity acts, and in such positioning, body movement is highly likely to occur again even in a case where re-imaging is performed. In contrast, in the simple imaging, the subject is irradiated with radiation once, and the imaging is less affected by body movement. For this reason, it is conceivable to perform the simple imaging at the time of re-imaging.

However, in a case where re-imaging is performed, it is necessary to perform the positioning of the subject again, such that it takes long time to complete the imaging. In particular, in a radiation image capturing apparatus (called mammography) for imaging a breast, it is necessary to perform imaging in a state where the breast is compressed, and thus the process causes pain of a patient as a subject. In a case where re-imaging is performed in such mammography, it is necessary to compress the breast again, and thus the process increases the burden on the patient.

SUMMARY OF THE INVENTION

The present disclosure has been made in view of the above situations, and an object thereof is to immediately perform re-imaging in a case where body movement occurs.

According to the present disclosure, there is provided an imaging control device comprising: an image acquisition unit that moves a radiation source relative to a detection unit and that acquires a plurality of projection images, which are generated by causing an imaging apparatus to perform tomosynthesis imaging for irradiating a subject with radiation under a first imaging condition for tomosynthesis imaging and which respectively correspond to a plurality of radiation source positions, at the plurality of radiation source positions obtained by movement of the radiation source; a body movement determination unit that determines whether or not body movement of the subject is occurring during the tomosynthesis imaging on the basis of the plurality of projection images; and a condition setting unit that sets a second imaging condition for simple imaging in the imaging apparatus in a case where the body movement is occurring.

The phrase "moves a radiation source relative to a detection unit" is defined to include all of a case of moving only the radiation source, a case of moving only the detection unit, and a case of moving both the radiation source and the detection unit.

The term "tomosynthesis imaging" is defined as an imaging method of moving the radiation source relative to the detection unit and acquiring the plurality of images, which respectively correspond to the plurality of radiation source positions, by irradiating the subject with radiation at the plurality of radiation source positions obtained by movement of the radiation source.

The term "simple imaging" is an imaging method of acquiring one image by irradiating the subject with radiation.

The imaging control device according to the present disclosure further comprises a reconstruction unit that reconstructs the plurality of projection images so as to generate a tomographic image on one tomographic plane of the subject. The body movement determination unit may detect at least one feature point from the tomographic image, calculate projection positions of the at least one feature point in the plurality of projection images, and determine whether or not the body movement is occurring on the basis of at least one of directions of movement or amounts of movement of the projection positions between the plurality of projection images.

In the imaging control device according to the present disclosure, the body movement determination unit may have a discriminator that learned to determine whether or not body movement is occurring on the basis of at least one of directions of movement or amounts of movement of various projection positions, input at least one of the directions of movement or the amounts of movement of the projection positions to the discriminator, and determine whether or not the body movement is occurring on the basis of an output of the discriminator.

In the imaging control device according to the present disclosure, the body movement determination unit may detect a plurality of feature points from the tomographic image, calculate projection positions in the plurality of projection images for each of the plurality of feature points, determine whether or not the body movement is occurring on the basis of at least one of the directions of movement or the amounts of movement of the projection positions between the plurality of projection images for each of the plurality of feature points, and determine whether or not the body movement is occurring on the basis of a determination result for each of the plurality of feature points.

In the imaging control device according to the present disclosure, the body movement determination unit may determine that the body movement is occurring in a case where a ratio of the number of the feature points, for which it is determined that the body movement is occurring, to the number of the plurality of feature points is equal to or greater than a predetermined threshold value.

In the imaging control device according to the present disclosure, the body movement determination unit may calculate a statistical value of output values of the discriminator at each of the plurality of feature points, and determine that the body movement is occurring in a case where the statistical value is equal to or greater than a predetermined threshold value.

In the imaging control device according to the embodiment of the present disclosure, the body movement determination unit may detect at least one correspondence point between the plurality of projection images, reconstructs a correspondence point between the plurality of projection images, specify at least one position of a structure indicating the correspondence point in the subject, calculate a projection position of the position of the structure in the plurality of projection images, calculate a distance between the correspondence point and the projection position in each of the plurality of projection images, and determine whether or not the body movement is occurring in accordance with whether or not a statistical value of the distances for the plurality of projection positions is equal to or greater than a predetermined threshold value.

In the imaging control device according to the embodiment of the present disclosure, the body movement determination unit may detect a plurality of correspondence points between the plurality of projection images, specify each of positions of a plurality of structures indicating the plurality of correspondence points in the subject for each of the plurality of correspondence points, calculate projection positions of the positions of the plurality of structures in the plurality of projection images, calculate each of distances between the correspondence points and the corresponding projection positions in the plurality of projection images for each of the plurality of correspondence points, determine whether or not a statistical value of the distances for correspondence points is equal to or greater than a predetermined threshold value for each of the plurality of projection images, and determine whether or not the body movement is occurring on the basis of a determination result of each of the plurality of correspondence points.

In the imaging control device according to the present disclosure, the body movement determination unit may determine that the body movement is occurring in a case where a ratio of the number of the correspondence points, for which it is determined that the body movement is occurring, to the number of the plurality of correspondence points is equal to or greater than a predetermined threshold value.

In the imaging control device according to the present disclosure, the body movement determination unit may further calculate, as a different statistical value, a statistical value of the statistical values of the distances for each of the plurality of correspondence points and determine that the body movement is occurring in a case where the different statistical value is equal to or greater than a predetermined threshold value.

The imaging control device according to the present disclosure may further comprise a notification unit that notifies that the simple imaging is to be performed in a case where the body movement is occurring.

In the imaging control device according to the present disclosure, the image acquisition unit may acquire a two-dimensional image of the subject, which is generated by causing the imaging apparatus to perform the simple imaging.

In the imaging control device according to the present disclosure, the first imaging condition and the second imaging condition may be different in terms of at least one of kinds of a target and a filter of the radiation source, a tube voltage of the radiation source, a dose of radiation from the radiation source, or presence or absence of a scattered radiation removal grid for removing a scattered radiation component included in the radiation transmitted through the subject.

In the imaging control device according to the present disclosure, the subject may be a breast.

According to the present disclosure, there is provided an imaging control method comprising: moving a radiation source relative to a detection unit and acquiring a plurality of projection images, which are generated by causing an imaging apparatus to perform tomosynthesis imaging for irradiating a subject with radiation under a first imaging condition for tomosynthesis imaging and which respectively correspond to a plurality of radiation source positions, at the plurality of radiation source positions obtained by movement of the radiation source; determining whether or not body movement of the subject is occurring during the tomosynthesis imaging on the basis of the plurality of projection images; and setting a second imaging condition for simple imaging in the imaging apparatus in a case where the body movement is occurring.

It should be noted that the imaging control method according to the present disclosure may be provided as a program for causing a computer to execute the imaging control method.

Another imaging control device according to the present disclosure comprises a memory for storing instructions to be executed by a computer and a processor configured to execute the stored instructions. The processor executes processes of: moving a radiation source relative to a detection unit and acquiring a plurality of projection images, which are generated by causing an imaging apparatus to perform tomosynthesis imaging for irradiating a subject with radiation under a first imaging condition for tomosynthesis imaging and which respectively correspond to a plurality of radiation source positions, at the plurality of radiation source positions obtained by movement of the radiation source; determining whether or not body movement of the subject is occurring during the tomosynthesis imaging on the basis of the plurality of projection images; and setting a second imaging condition for simple imaging in the imaging apparatus in a case where the body movement is occurring.

According to the present disclosure, the plurality of projection images, which are generated by causing the imaging apparatus to perform tomosynthesis imaging and which respectively corresponds to the plurality of radiation source positions under the first imaging condition for tomosynthesis imaging, are acquired, and it is determined whether or not body movement of the subject is occurring during the tomosynthesis imaging on the basis of the plurality of projection images. Then, in a case where a body movement is occurring, the second imaging condition for simple imaging is set in the imaging apparatus. For this reason, in a case where the body movement is occurring at the time of tomosynthesis imaging, simple imaging can be immediately performed without performing the positioning of the subject again. Therefore, it is possible to reduce the burden on the patient as a subject in a case where body movement occurs.

DETAILED DESCRIPTION

Figure 1:
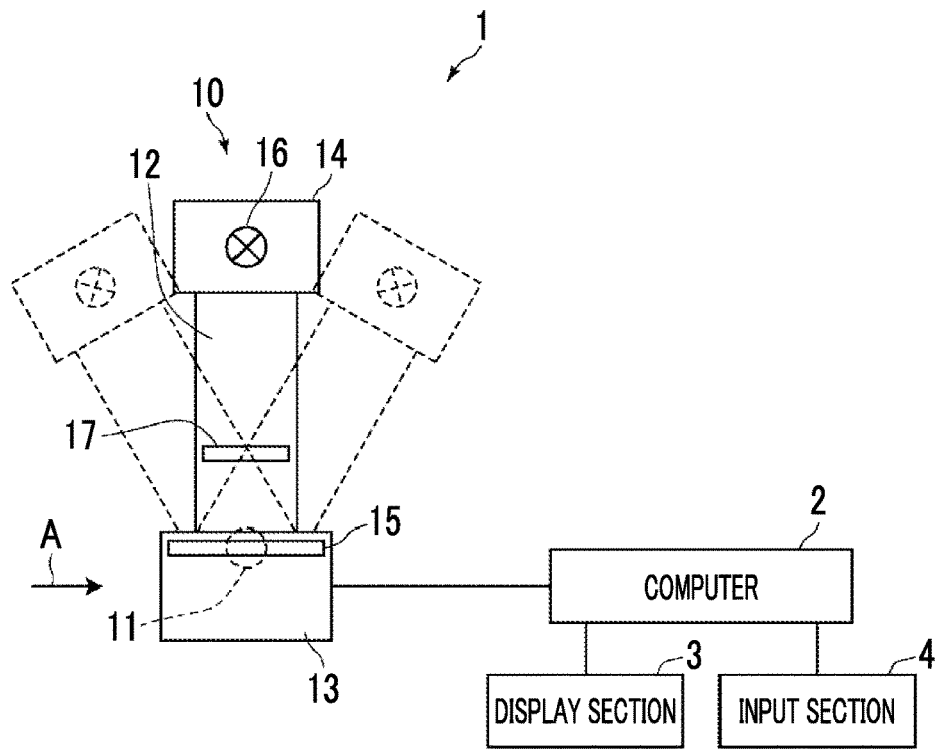
FIG. 1 is a schematic configuration diagram of a radiation image capturing apparatus to which an imaging control device according to a first embodiment of the present disclosure is applied.
Figure 2:
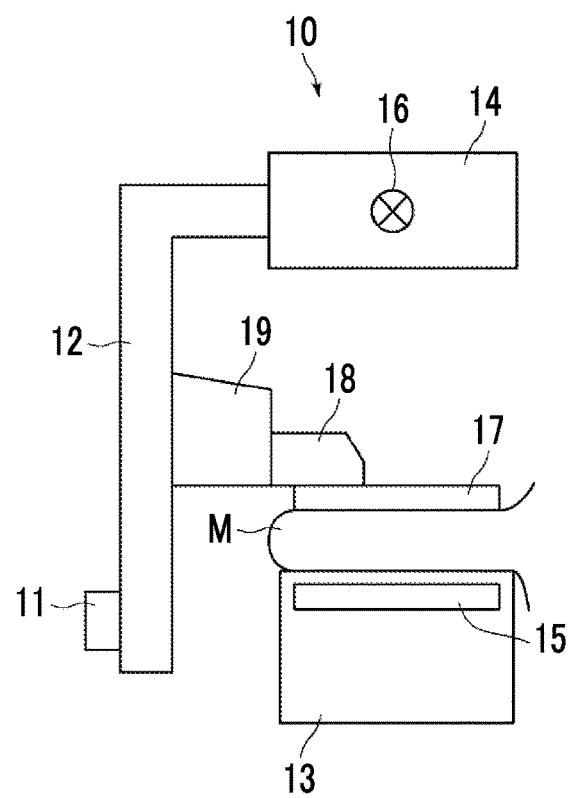
FIG. 2 is a view of the radiation image capturing apparatus as viewed from a direction of arrow A in FIG. 1.

Hereinafter, embodiments of the present disclosure will be described with reference to the drawings. FIG. 1 is a schematic configuration diagram of a radiation image capturing apparatus to which an imaging control device according to a first embodiment of the present disclosure is applied. FIG. 2 is a view of the radiation image capturing apparatus as viewed from a direction of arrow A in FIG. 1. A radiation image capturing apparatus 1 is a mammography imaging apparatus that captures images of a breast M as a subject from a plurality of radiation source positions and acquires a plurality of radiation images, that is, a plurality of projection images in order to generate a tomographic image by performing tomosynthesis imaging on a breast. As shown in FIG. 1, the radiation image capturing apparatus 1 comprises an imaging unit 10, a computer 2 connected to the imaging unit 10, and a display unit 3 and an input unit 4 connected to the computer 2. In addition to the tomosynthesis imaging, the radiation image capturing apparatus 1 according to the present embodiment also performs simple imaging as will be described later, and also acquires a two-dimensional image of the breast M.

The imaging unit 10 comprises an arm unit 12 connected to a base, which is not shown, by a rotation shaft 11. An imaging table 13 is attached to one end of the arm unit 12, and a radiation irradiation unit 14 is attached to the other end so as to face the imaging table 13. The arm unit 12 is configured so as to be able to rotate only the end portion to which the radiation irradiation unit 14 is attached, such that it becomes possible to rotate only the radiation irradiation unit 14 with the imaging table 13 fixed. The computer 2 controls the rotation of the arm unit 12.

A radiation detector 15 such as a flat panel detector is provided inside the imaging table 13. Inside the imaging table 13, the following elements are provided: a charge amplifier that converts a charge signal read from the radiation detector 15 into a voltage signal; a sampling two correlation pile circuit that samples a voltage signal output from the charge amplifier; a circuit board that is provided with an A/D converter which converts a voltage signal into a digital signal; and the like. The radiation detector 15 corresponds to the detection unit.

The radiation detector 15 is able to repeatedly perform recording and reading of a radiation image. As the radiation detector 15, a so-called direct type radiation detector, which is directly irradiated with radiation so as to generate electric charge, may be used, and a so-called indirect type radiation detector, which converts radiation into visible light once and converts the visible light into a charge signal, may be used.

As a method of reading the radiation image signal, it is preferable to use a so-called thin film transistor (TFT) reading type, in which a radiation image signal is read by turning on and off a TFT switch, or a so-called optical reading type, in which a radiation image signal is read by performing irradiation of the light to be read. However, the method is not limited to this, and other methods may be used.

In the inside of the radiation irradiation unit 14, an X-ray source 16 as a radiation source is stored. The computer 2 controls timing of emitting the X-ray as the radiation from the X-ray source 16, an X-ray generation conditions in the X-ray source 16 such as selection of materials of a target and a filter, a tube voltage, and an irradiation time.

Further, on the arm unit 12, a compression plate 17 that is disposed above the imaging table 13 to forcibly press the breast M, a support unit 18 that supports the compression plate 17, and a movement mechanism 19 that moves the support unit 18 in the vertical direction of FIGS. 1 and 2. The distance between the compression plate 17 and the imaging table 13, that is, the compression thickness is input to the computer 2.

The display unit 3 is a display device such as a cathode ray tube (CRT) or a liquid crystal monitor, and displays a projection image and a two-dimensional image acquired as described later, a generated tomographic image, a message necessary for an operation, or the like. It should be noted that the display unit 3 may incorporate a speaker that outputs sound.

The input unit 4 includes a keyboard, a mouse, or a touch panel type input device, and accepts an operation of the radiation image capturing apparatus 1 performed by an operator. Further, the input unit 4 accepts various information pieces, such as imaging conditions, necessary for performing tomosynthesis imaging, and instructions for correcting the information pieces. In the present embodiment, each unit of the radiation image capturing apparatus 1 operates in accordance with the information which is input by the operator from the input unit 4.

In the computer 2, an imaging control program according to the present embodiment is installed. In the present embodiment, the computer may be a work station or a personal computer directly operated by the operator, or may be a server computer connected to those through a network. The imaging control program is distributed in a state where the program is recorded on a recording medium such as a digital versatile disc (DVD) or a compact disc read only memory (CD-ROM), and the program is installed on the computer from the recording medium. Alternatively, the imaging control program is stored in a network storage or a storage device of a server computer connected to a network in an accessible state from the outside, downloaded to a computer in response to a request, and installed.

Figure 3:
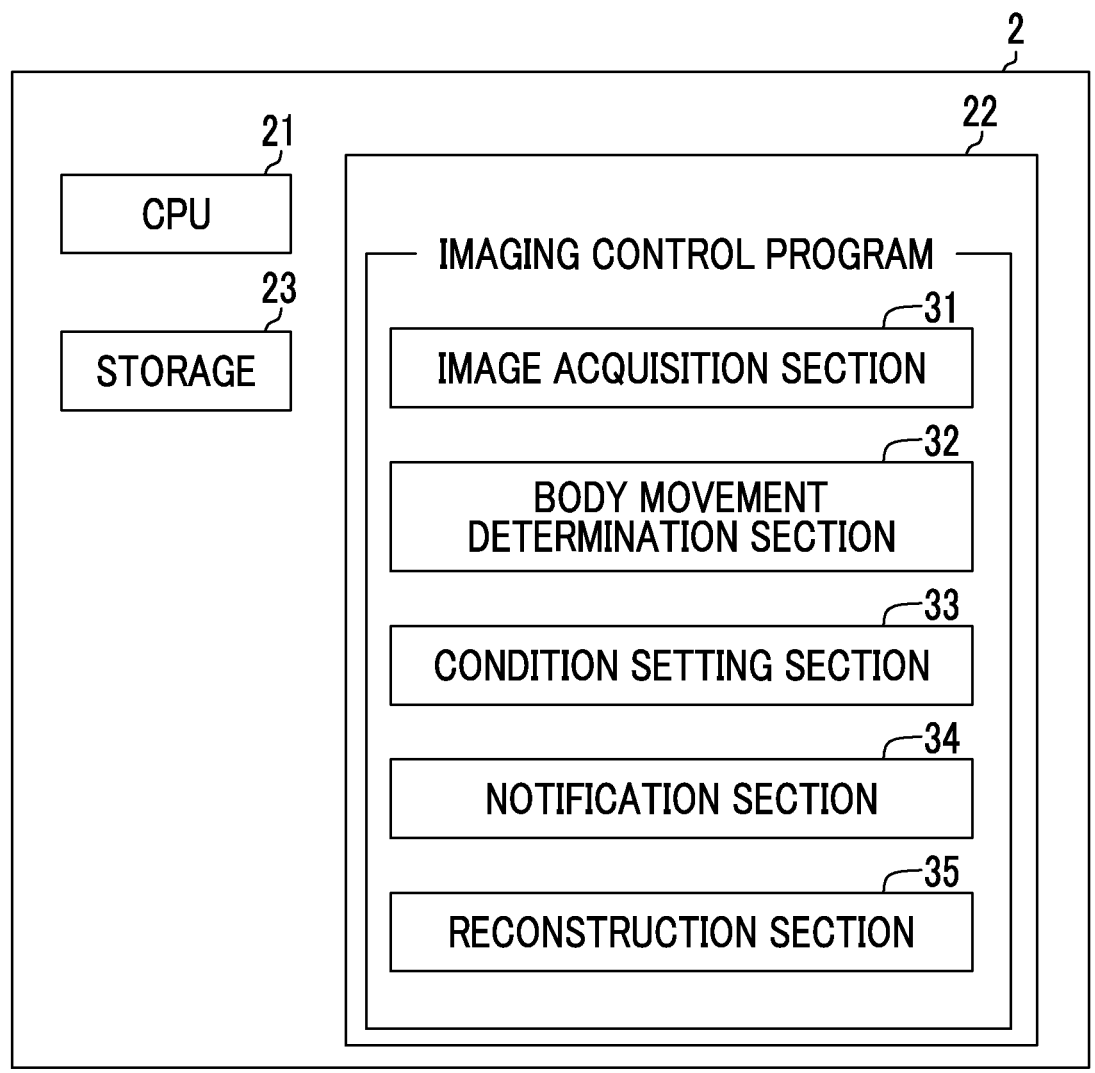
FIG. 3 is a diagram showing a schematic configuration of the imaging control device implemented by installing an imaging control program in a computer in the first embodiment.

FIG. 3 is a diagram showing a schematic configuration of the imaging control device implemented by installing the imaging control program in the computer 2. As shown in FIG. 3, the imaging control device comprises a central processing unit (CPU) 21, a memory 22, and a storage 23 as a standard computer configuration.

The storage 23 includes a storage device such as a hard disk or a solid state drive (SSD), and stores various information pieces including a program for driving each unit of the radiation image capturing apparatus 1 and an imaging control program. In addition, a projection image acquired by tomosynthesis imaging, a two-dimensional image acquired by simple imaging, and a tomographic image generated as described later are also stored.

The memory 22 temporarily stores a program and the like stored in the storage 23 so as to cause the CPU 21 to execute various kinds of processing. As the processing to be executed by the CPU 21, the imaging control program defines first image acquisition processing, body movement determination processing, condition setting processing, notification processing, second image acquisition processing, and reconstruction processing. The first image acquisition processing is processing of acquiring a plurality of projection images of the breast M respectively corresponding to a plurality of radiation source positions by causing the radiation image capturing apparatus 1 to perform tomosynthesis imaging under a first imaging condition for tomosynthesis imaging. The body movement determination processing is processing of determining whether or not body movement of a breast M as a subject is occurring during tomosynthesis imaging, on the basis of a plurality of projection images. The condition setting processing is processing of setting the first imaging condition for tomosynthesis imaging and the second imaging condition for simple imaging in the radiation image capturing apparatus 1, and in a case where body movement is occurring. The notification processing is processing of giving notification that simple imaging is to be performed in a case where body movement is occurring. The second image acquisition processing is processing of causing the radiation image capturing apparatus 1 to perform simple imaging to acquire a two-dimensional image of the breast M. The reconstruction processing is processing of generating a tomographic image of a tomographic plane of the breast M by reconstructing the plurality of projection images.

Then, the CPU 21 executes these kinds of processing in accordance with the imaging control program, such that the computer 2 functions as an image acquisition unit 31, a body movement determination unit 32, a condition setting unit 33, a notification unit 34, and a reconstruction unit 35. It should be noted that the image acquisition unit 31 performs both the first image acquisition processing and the second image acquisition processing described above.

In the present embodiment, the CPU 21 executes the functions of the respective units through the imaging control program. However, as a general-purpose processor that executes software and functions as various processing units, in addition to the CPU 21, it is possible to use a programmable logic device (PLD) which is a processor capable of manufacturing a field programmable gate array (FPGA) or the like and thereafter changing a circuit configuration thereof. In addition, processing of each unit may be executed by a dedicated electric circuit or the like which is a processor having a circuit configuration designed exclusively for executing specific processing of an application specific integrated circuit (ASIC) or the like.

One processing unit may be configured as one of these various processors, or may be configured as a combination of two or more of the same or different types of processors (for example, a plurality of FPGAs, a combination of a CPU and an FPGA, or the like). Further, a plurality of processing units may be configured as one processor. As an example of configuring a plurality of processing units as one processor, first, there is a configuration in which one processor is configured as a combination of one or more CPUs and software as typified by a computer such as a client and a server such that this processor functions as the plurality of processing units. Second, as typified by a system on chip (SoC) or the like, there is a configuration using a processor in which the function of the whole system including the plurality of processing units is implemented by one integrated circuit (IC) chip. In such a manner, the various processing units are configured using one or more of the above-mentioned various processors as a hardware structure.

Further, the hardware structure of these various processors is more specifically an electric circuit (circuitry) in which circuit elements such as semiconductor elements are combined.

Figure 4:
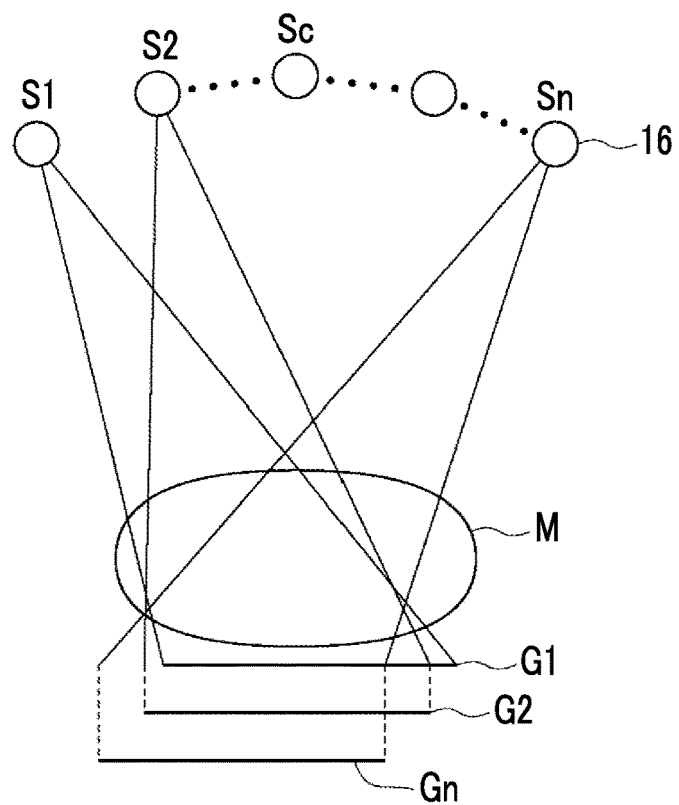
FIG. 4 is a diagram for explaining acquisition of projection images.

At the time of performing the first image acquisition processing, the image acquisition unit 31 moves the X-ray source 16 by rotating the arm unit 12 around the rotation shaft 11, irradiates the breast M as a subject with X-rays under a first imaging condition for tomosynthesis imaging at the plurality of radiation source positions set by the movement of the X-ray source 16, detects the X-rays transmitted through the breast M through the radiation detector 15, and acquires a plurality of projection images Gi (i=1 to n, where n is the number of radiation source positions, for example n=15) at the plurality of radiation source positions. FIG. 4 is a diagram for explaining the acquisition of the projection images Gi. As shown in FIG. 4, the X-ray source 16 is moved to each radiation source position of S1, S2, . . . Sn, the X-ray source 16 is driven at each radiation source position to irradiate the breast M with X-ray, and the radiation detector 15 detects the X-rays transmitted through the breast M. Thereby, the projection images G1, G2, . . . Gn are acquired corresponding to the respective radiation source positions S1 to Sn. At each of the radiation source positions S1 to Sn, the breast M is irradiated with X-rays having the same dose. The plurality of acquired projection images Gi is stored in the storage 23. Further, the plurality of projection images Gi may be acquired by a program separate from the imaging control program and may be stored in the storage 23. In this case, the image acquisition unit 31 reads the plurality of projection images Gi stored in the storage 23 from the storage 23 for reconstruction processing or the like.

In FIG. 4, the radiation source position Sc is a radiation source position at which the optical axis of the X-ray from the X-ray source 16 is orthogonal to the radiation detector 15.

Figure 5:
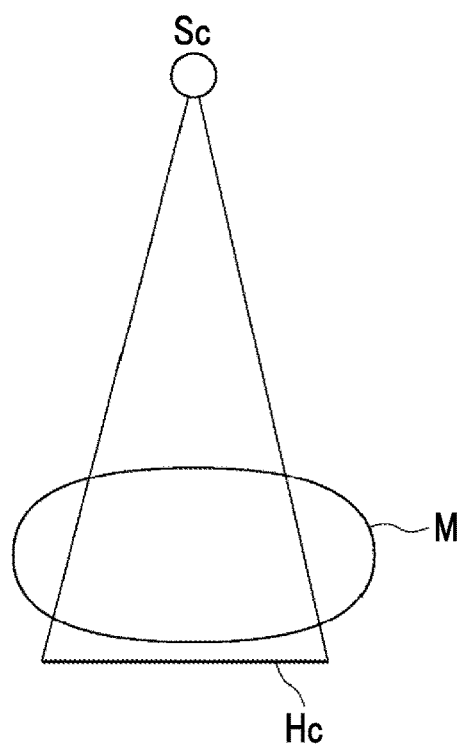
FIG. 5 is a diagram for explaining acquisition of a two-dimensional image.
Figures 6, 7:
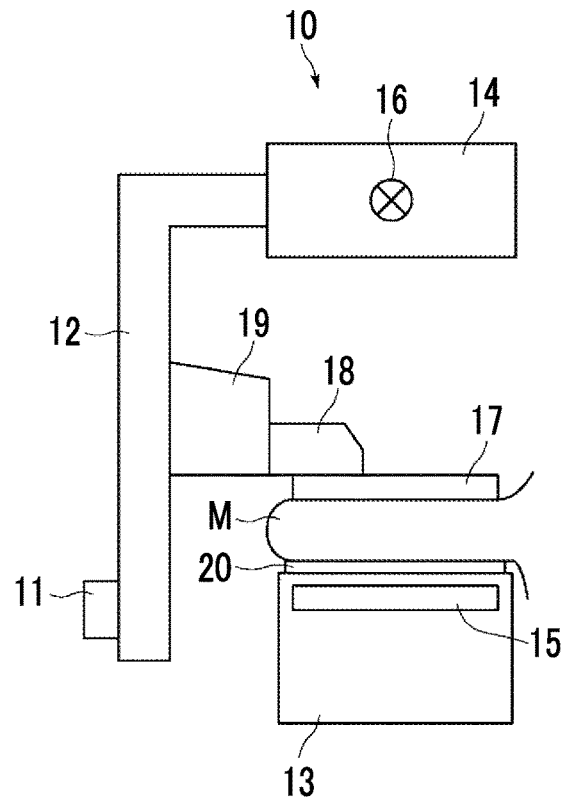
FIG. 6 is a view of the radiation image capturing apparatus as viewed from the direction of arrow A in FIG. 1 at the time of acquiring the two-dimensional image.
FIG. 7 is a diagram showing a table of imaging conditions.

The image acquisition unit 31 causes the radiation image capturing apparatus 1 to perform the second image acquisition processing to acquire the two-dimensional image Hc. FIG. 5 is a diagram for explaining the acquisition of the two-dimensional image Hc. As shown in FIG. 5, the second image acquisition unit 31 acquires the two-dimensional image Hc which is a two-dimensional radiation image by rotating the arm unit 12 around the rotation shaft 11 so as to move the X-ray source 16 to the radiation source position Sc, irradiating the breast M as a subject with X-rays under the second imaging condition for simple imaging at the radiation source position Sc, and detecting the X-rays transmitted through the breast M through the radiation detector 15. The acquired two-dimensional image Hc is stored in the storage 23. In a case of performing simple imaging, as shown in FIG. 6, an anti-scatter grid 20 (hereinafter, simply referred to as a grid) for removing scattered rays transmitted through the breast M is disposed between the breast M and the radiation detector 15, in accordance with the second imaging condition. In a case of performing tomosynthesis imaging, the grid 20 is not disposed as shown in FIG. 2 in accordance with the first imaging condition described later. In a case where the grid 20 is disposed, the compression thickness is a distance between the upper surface of the grid 20 and the compression plate 17. Further, the two-dimensional image Hc may be acquired by a program separate from the imaging control program and may be stored in the storage 23.

The body movement determination unit 32 determines whether or not body movement of the breast M as a subject is occurring during tomosynthesis imaging. The body movement determination processing performed by the body movement determination unit 32 will be described later.

The condition setting unit 33 sets the first imaging condition for tomosynthesis imaging and the second imaging condition for simple imaging in the radiation image capturing apparatus 1. Specifically, the condition setting unit 33 sets the first imaging condition in the radiation image capturing apparatus 1 at the time of tomosynthesis imaging. In a case where the body movement determination unit 32 determines that the body movement of the breast M as a subject is occurring during tomosynthesis imaging, the condition setting unit 33 sets the second imaging condition in the radiation image capturing apparatus 1.

Hereinafter, the first and second imaging conditions will be described. The X-ray source 16 comprises a filament for outputting an electron beam, a target for generating X-rays through collision of an electron beam, and a filter for adjusting an energy spectrum of X-rays. The target has a plurality of different anode materials, for example, molybdenum (Mo), rhodium (Rh) and tungsten (W), and these are selectively arranged. The filter has a plurality of different substances, for example molybdenum (Mo), rhodium (Rh), tungsten (W), and aluminum (Al), and these are selectively arranged.

The imaging condition is a condition for obtaining an appropriate radiation image by adjusting the energy spectrum (line quality) of the X-rays to be emitted to the breast M. For example, the imaging condition includes an X-ray generation condition and a grid condition. The X-ray generation condition consists of a kind of target constituting the X-ray source 16, a kind of filter, and the tube voltage applied between the filament and the target. The grid condition indicates presence or absence of the grid 20. It should be noted that the mAs value (tube current×radiation irradiation time) may be included as imaging conditions.

In the present embodiment, an imaging condition table for each of the tomosynthesis imaging and the simple imaging is stored in the storage 23. FIG. 7 is a diagram showing a table of imaging conditions. As shown in FIG. 7, a table LUT1 for imaging conditions defines imaging conditions corresponding to a plurality of breast thicknesses. Specifically, T/F indicating the kinds of target and filter, the tube voltage, and presence or absence of the grid are set. It should be noted that IN indicates presence of the grid and OUT indicates absence of the grid. By referring to the table LUT1, for example, in a case where the thickness of the breast is 45 mm, at the time of tomosynthesis imaging, T/F is set as W/Al (the target is W, and the filter is Al), the tube voltage is set to 32 kV, and absence of the grid is set as the first imaging condition. At the time of simple imaging, T/F is set as W/Rh (the target is W, and the filter is Rh), the tube voltage is set to 29 kV, and presence of the grid is set as the second imaging condition. Further, moving the X-ray source 16 to the radiation source position Sc is also set as the second imaging condition.

In a case where the body movement determination unit 32 determines that body movement is occurring at the time of tomosynthesis imaging, the notification unit 34 notifies that simple imaging is to be performed. Specifically, for example, by displaying the text "perform simple imaging" on the display unit 3, notification that simple imaging is to be performed is given. It should be noted that notification may be given by displaying an icon for performing simple imaging or the like on the display unit 3. In addition, the notification unit 34 may give the notification by outputting sound indicating that simple imaging is to be performed. At this time, the condition setting unit 33 sets the second imaging condition for simple imaging in the radiation image capturing apparatus 1. Therefore, the operator merely gives instruction for imaging from the input unit 4 so as to instantly perform simple imaging of the breast M, whereby it is possible to acquire the two-dimensional image Hc.

By reconstructing the projection images Gi, the reconstruction unit 35 generates a tomographic image in which a desired tomographic plane of the breast M is emphasized. Specifically, the reconstruction unit 35 reconstructs the projection images Gi using a well-known back projection method such as a simple back projection method or a filtered back projection method, thereby generating a tomographic image for each of the plurality of tomographic planes of the breast M.

Figure 8:
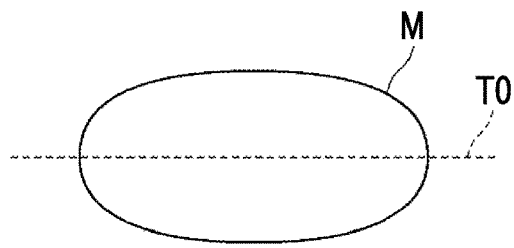
FIG. 8 is a diagram showing a tomographic plane for generating a tomographic image.

Hereinafter, the body movement determination processing performed by the body movement determination unit 32 will be described. In the first embodiment, the body movement determination unit 32 performs the body movement determination processing using the tomographic image generated by the reconstruction unit 35. Therefore, in the first embodiment, the body movement determination unit 32 instructs the reconstruction unit 35 to reconstruct the projection images Gi and generate a tomographic image. In order to determine the body movement, tomographic images on a plurality of tomographic planes are not necessary, and only one tomographic image on one tomographic plane may be generated. In the first embodiment, as shown in FIG. 8, it is assumed that a tomographic image D0 on a tomographic plane T0 at which a compression thickness is ½ is generated.

Next, the body movement determination unit 32 detects a feature point from the tomographic image D0. Specifically, at least one feature point of an edge, an edge intersection, an edge corner, or the like included in the tomographic image D0 is detected using an algorithm such as the Harris's corner detection method, the scale-invariant feature transform (SIFT), the features from accelerated segment test (FAST), or the speeded up robust features (SURF). In this description, it is assumed that only one feature point is detected. Then, the body movement determination unit 32 calculates the projection positions of the feature point in the projection images Gi. It should be noted that the feature point may be only one pixel in the tomographic image D0 or may consist of a plurality of pixels indicating the position of the characteristic structure.

Figure 9:
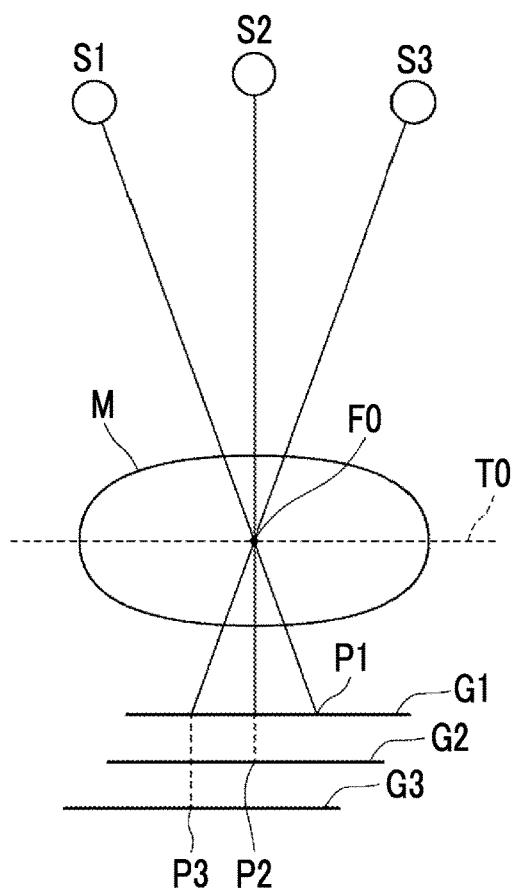
FIG. 9 is a diagram for explaining calculation of projection positions of a feature point from projection images.

FIG. 9 is a diagram for explaining the calculation of the projection positions of the feature point from the projection images. In FIG. 9, in order to simplify the explanation, the calculation of the projection positions from three projection images G1 to G3 corresponding to three radiation source positions S1 to S3 will be described. Further, in FIG. 9, the projection images G1 to G3 are shown to be present on different planes for the sake of explanation, but are actually present on the same plane. Further, in FIG. 9, it is assumed that the feature point F0 is detected in the tomographic image D0. Therefore, the tomographic plane T0 includes the feature point F0. As shown in FIG. 9, at the time of imaging, the feature point F0 included in the tomographic plane T0 of the breast M is projected onto positions P1 to P3 in the respective projection images G1 to G3. The radiation source positions S1 to S3 and the position of the feature point F0 in the breast M in the three-dimensional space are given. In addition, the position of the detection surface of the radiation detector 15 where the projection images G1 to G3 are generated is also given. Therefore, the body movement determination unit 32 calculates the projection positions P1 to P3 of the feature point F0 in the projection images G1 to G3, on the basis of the radiation source positions S1 to S3, the position of the feature point F0 in the breast M in three-dimensional space, and the position of the detection surface of the radiation detector 15 where the projection images G1 to G3 are generated.

Figure 10:
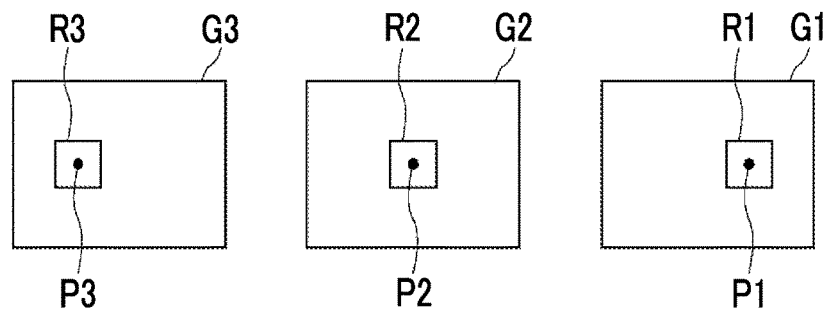
FIG. 10 is a diagram for explaining setting of a region of interest.

Subsequently, as shown in FIG. 10, the body movement determination unit 32 sets regions of interest R1 to R3, which have a predetermined size and are centered on the projection positions P1 to P3, in the projection images G1 to G3. Further, the body movement determination unit 32 performs registration between the regions of interest R1 to R3 in the adjacent projection images, and calculates shift vectors indicating the directions of movement and the amounts of movement between the regions of interest in the adjacent projection images. It should be noted that the number of shift vectors is one less than the number of projection images. For example, in a case where the number of projection images is 15, the number of shift vectors is 14, and in a case where the number of projection images is 3, the number of shift vectors is 2.

Figure 11:
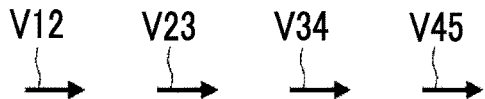
FIG. 11 is a diagram showing shift vectors in a case where no body movement is occurring.
Figure 12:
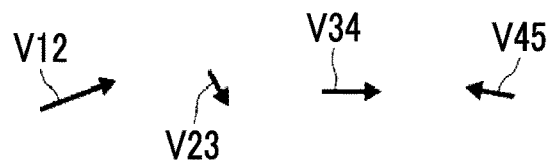
FIG. 12 is a diagram showing shift vectors in a case where body movement is occurring.

FIG. 11 is a diagram showing shift vectors in a case where no body movement is occurring. FIG. 12 is a diagram showing shift vectors in a case where body movement is occurring. FIGS. 11 and 12 show four shift vectors V12, V23, V34, and V45 calculated in the five projection images G1 to G5 for explanation. Further, in FIGS. 11 and 12, the horizontal direction in the drawing is the direction of movement of the X-ray source 16. In the case where no body movement is occurring, as shown in FIG. 11, the shift vectors V12, V23, V34, and V45 are substantially constant in size and are oriented in the direction of movement of the X-ray source 16. Alternatively, the magnitudes of the shift vectors V12, V23, V34, and V45 are substantially zero. On the other hand, in a case where body movement is occurring, as shown in FIG. 12, the shift vectors V12, V23, V34, and V45 are oriented in irregular directions and are irregular in size.

In the first embodiment, for example, an artificial intelligence (AI) technology can be applied to the processing of determining whether or not body movement is occurring. Specifically, the shift vectors are input, and a deep neural network whose output is presence or absence of body movement is created. Next, a discriminator is stored in the storage 23. The discriminator is formed of a learned model obtained by learning the created deep neural network on the basis of the shift vectors and teaching data including presence or absence of occurrence of body movement due to the shift vectors. The body movement determination unit 32 determines whether or not body movement is occurring by inputting the calculated shift vectors to the discriminator and acquiring information indicating the presence or absence of body movement output from the discriminator. For example, using the learned model, in which the learning is performed such that an output value between −1 and +1 is output, as a discriminator, it is determined that body movement is occurring in a case where the output of the discriminator becomes equal to or greater than 0. The body movement determination unit 32 may store the discriminator.

Figure 13:
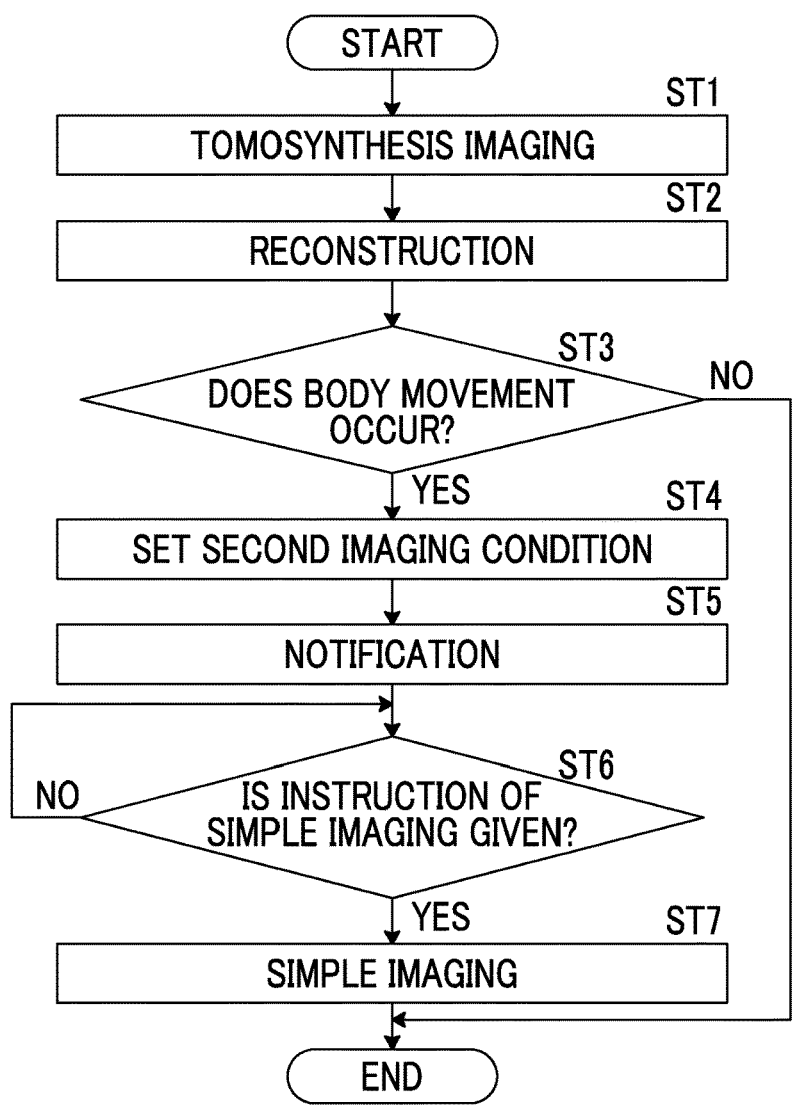
FIG. 13 is a flowchart showing a process performed in the first embodiment.

Next, processing performed in the first embodiment will be described. FIG. 13 is a flowchart showing processing performed in the first embodiment. In this embodiment, since tomosynthesis imaging is first performed, the condition setting unit 33 sets the first imaging condition in the radiation image capturing apparatus 1. In a case where the input unit 4 accepts instruction to start processing issued by the operator, the image acquisition unit 31 causes the radiation image capturing apparatus 1 to perform tomosynthesis imaging under the first imaging condition, and performs the first image acquisition processing of acquiring the plurality of projection images Gi (step ST1). Then, the reconstruction unit 35 reconstructs the plurality of projection images Gi to generate tomographic images on a plurality of tomographic planes of the breast M (step ST2). The plurality of projection images Gi and the generated tomographic images are stored in the storage 23. Next, the body movement determination unit 32 determines whether or not body movement of the breast M is occurring during tomosynthesis imaging (step ST3). In a case where the body movement is occurring (step ST3; YES), the condition setting unit 33 sets the second imaging condition for simple imaging in the radiation image capturing apparatus 1 (step ST4), and the notification unit 34 gives notification that simple imaging is to be performed (step ST5). It should be noted that the processing of step ST5 may be performed before step ST4 or the processing of steps ST4 and ST5 may be performed at the same time.

The image acquisition unit 31 starts monitoring whether or not instruction for simple imaging has been given from the input unit 4 (step ST6). In a case where the result in step ST6 is positive, the image acquisition unit 31 performs the second image acquisition processing of acquiring the two-dimensional image Hc by performing simple imaging on the radiation image capturing apparatus 1 (step ST7), and the processing ends. It should be noted that the acquired two-dimensional image Hc is stored in the storage 23 in association with the tomographic image.

On the other hand, in a case where no body movement is occurring (step ST3; NO), the processing ends. In a case where the processing ends, compression of the breast M by the compression plate 17 is released.

As described above, in the first embodiment, a plurality of projection images Gi are acquired under the first imaging condition for tomosynthesis imaging, and it is determined whether or not body movement of the breast M as a subject is occurring during tomosynthesis imaging, on the basis of the plurality of projection images Gi. Then, in a case where body movement is occurring, the second imaging condition for simple imaging is set in the radiation image capturing apparatus 1. Therefore, in a case where body movement is occurring at the time of tomosynthesis imaging, simple imaging can be immediately performed without performing positioning of the breast M as a subject again. In addition, the notification unit 34 gives notification that simple imaging is to be performed, and thus the operator can immediately perform simple imaging on the basis of the notification. Therefore, according to the present embodiment, it is possible to reduce a burden on a patient as a subject in a case where body movement occurs.

In the first embodiment, the body movement determination unit 32 detects one feature point from the tomographic image and determines whether or not body movement is occurring. However, the present invention is not limited to this. The body movement determination unit 32 may detect a plurality of feature points from the tomographic image, calculate shift vectors of the projection positions by detecting the projection positions of the projection images Gi for each of the plurality of feature points, and determine whether or not body movement is occurring on the basis of the shift vectors of the plurality of feature points.

In this case, the body movement determination unit 32 determines whether or not body movement is occurring at each of the plurality of feature points, on the basis of the output value of the discriminator at each of the plurality of feature points, and calculates a ratio of the number of feature points, for which it is determined that body movement is occurring, to the number of the plurality of feature points. Then, in a case where the calculated ratio is predetermined and equal to or greater than a predetermined threshold value Th1, the body movement determination unit 32 may determine that body movement is occurring. The threshold value Th1 may be set to 0.5, for example, but the present invention is not limited to this.

As another method of determining whether or not body movement is occurring on the basis of the shift vectors for the plurality of feature points, the body movement determination unit 32 calculates a statistical value of the output values of the discriminator for each of the plurality of feature points. As the statistical value, an average value, a median value, a maximum value, a minimum value, or the like of outputs of the discriminator can be used. Then, in a case where the calculated statistical value is equal to or greater than a predetermined threshold value Th2, the body movement determination unit 32 may determine that body movement is occurring. The threshold value Th2 may be set to 0, for example, in a case where the output of the discriminator is a value between −1 and 1, but the present invention is not limited to this.

In the first embodiment, the region of interest is set at the projection position of the feature point, and the direction of movement and the amount of movement of the region of interest are calculated as shift vectors, but the present invention is not limited to this. The directions of movement and the amounts of movement between the projection images of the projection positions of the feature points may be calculated as shift vectors without setting the regions of interest.

In the first embodiment, it is determined whether or not body movement is occurring on the basis of shift vectors indicating the directions of movement and the amounts of movement of the regions of interest (or the projection positions of the feature points). However, the present invention is not limited to this. The body movement determination unit 32 may determine whether or not body movement is occurring on the basis of only the directions of movement. In this case, in a case where the directions of movement of the projection positions of the feature points between the projection images are irregular, it may be determined that body movement is occurring. Further, it may be determined whether or not body movement is occurring on the basis of only the amounts of movement. In this case, in a case where the amount of movement is greater than the predetermined threshold value, it may be determined that body movement is occurring.

Next, a second embodiment of the present disclosure will be described. The configuration of the imaging control device according to the second embodiment is the same as the configuration of the imaging control device according to the first embodiment, and only the processing performed by the body movement determination unit 32 is different. Therefore, in this embodiment, detailed description of the configuration will be omitted. Hereinafter, the body movement determination processing in the imaging control device of the second embodiment will be described.

In the second embodiment, the body movement determination unit 32 first detects a correspondence point that is a common structure included in a plurality of projection images Gi. Specifically, similarly to the detection of the feature point F0 from the tomographic image D0 in the first embodiment, at least one correspondence point is detected by using an algorithm such as Harris's corner detection method, SIFT, FAST, or SURF. The correspondence point includes structures between the projection images Gi such as the edge, the intersection of the edge, and the corner portion of the edge included in the projection images Gi. In this description, it is assumed that one correspondence point is detected.

Figure 14:
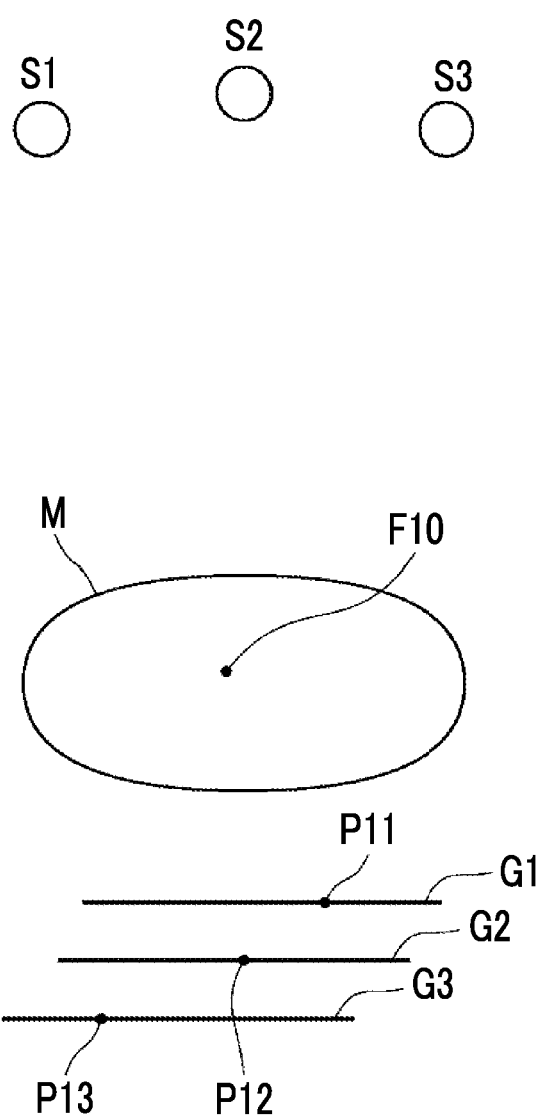
FIG. 14 is a diagram for explaining calculation of a position of a structure in a three-dimensional space indicated by correspondence points in a breast.

Next, the body movement determination unit 32 back-projects the correspondence points detected in the projection images Gi to calculate the position of the structure in the three-dimensional space indicated by the correspondence points in the breast M. FIG. 14 is a diagram for explaining the calculation of the position of the structure in the three-dimensional space indicated by the correspondence points in the breast M. In FIG. 14, in order to simplify the explanation, calculation of the position of the structure in the three-dimensional space using the three projection images G1 to G3 corresponding to the three radiation source positions S1 to S3 will be described. Further, in FIG. 14, the projection images G1 to G3 are shown to be present on different planes for the sake of explanation, but are actually present on the same plane.

As shown in FIG. 14, the correspondence point P11 in the projection image G1, the correspondence point P12 in the projection image G2, and the correspondence point P13 in the projection image G3 are back-projected. Thereby, the position F10 of the structure indicated by the correspondence points P11, P12, and P13 in the breast M is specified. Through back projection, it is possible to calculate a tomographic plane where the position F10 of the structure is present and a two-dimensional position in the tomographic plane. As a result, it is possible to calculate the coordinate position of the position F10 of the structure in the three-dimensional space.

Figure 15:
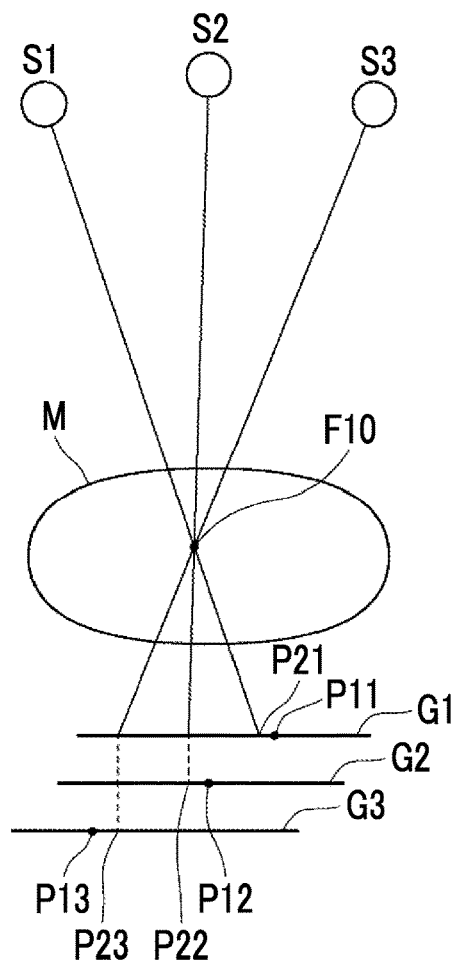
FIG. 15 is a diagram for explaining the calculation of the projection positions of the structure.

In the second embodiment, the body movement determination unit 32 further calculates the projection positions P21, P22, and P23 on the projection images G1 to G3 of the position F10 of the structure. FIG. 15 is a diagram for explaining the calculation of the projection positions of the position F10 of the structure. In FIG. 15, in order to simplify the explanation, the calculation of the projection positions of the position F10 of the structure from the three projection images G1 to G3 corresponding to the three radiation source positions S1 to S3 will be described. Further, in FIG. 15, the projection images G1 to G3 are shown to be present on different planes for the sake of explanation, but are actually present on the same plane. As shown in FIG. 15, the position F10 of the structure is projected to positions P21 to P23 in the respective projection images G1 to G3. The radiation source positions S1 to S3 and the position F10 of the structure in the three-dimensional space are given. In addition, the position of the detection surface of the radiation detector 15 where the projection images G1 to G3 are generated is also given. Therefore, the body movement determination unit 32 calculates the projection positions P21 to P23 of the position F10 of the structure in the projection images G1 to G3, on the basis of the radiation source positions S1 to S3, the position F10 of the structure in the three-dimensional space, and the position of the detection surface of the radiation detector 15 where the projection images G1 to G3 are generated.

Figure 16:
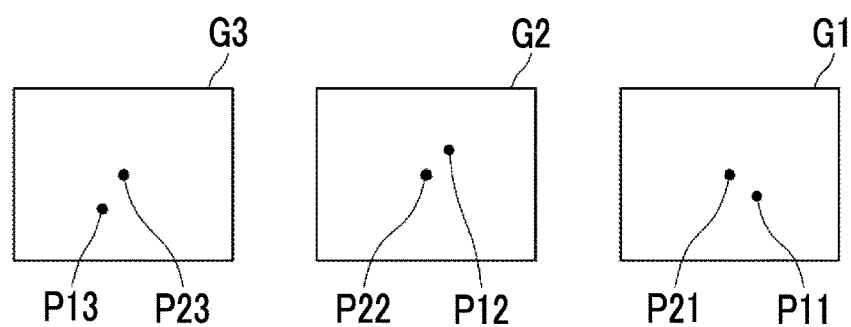
FIG. 16 is a diagram showing states in which the projection positions and the correspondence points are deviated from each other.

It should be noted that the projection position P21 of the position F10 of the structure and the correspondence point P11 in the projection image G1 may coincide with each other or may not coincide with each other. The projection position P22 of the position F10 of the structure and the correspondence point P12 in the projection image G2 and the projection position P23 of the position F10 of the structure and the correspondence point P13 in the projection image G3 may coincide with each other or may deviate from each other. FIG. 15 shows a situation where the projection position P21 and the correspondence point P11, the projection position P22 and the correspondence point P12, and the projection position P23 and the correspondence point P13 deviate from each other. FIG. 16 is a diagram showing a state where the projection position P21 and the correspondence point P11, the projection position P22 and the correspondence point P12, and the projection position P23 and the correspondence point P13 deviate from each other.

The body movement determination unit 32 calculates a magnitude of the deviation between the correspondence point and the projection position in each of the projection images Gi. Then, a statistical value of the magnitudes of the deviation for all the projection images Gi is calculated. As the statistical value, an average value, a median value, a maximum value, a minimum value, or the like can be used. Then, the body movement determination unit 32 compares the statistical value with a predetermined threshold value Th3, and determines that body movement is occurring in a case where the statistical value is greater than the threshold value Th3. As the threshold value Th3, it is possible to use experimentally calculated values that can be regarded as body movement occurring in a case where the statistical value is greater than the threshold value Th3.

By determining whether or not body movement is occurring in the body movement determination unit 32 as in the second embodiment, in a case where body movement is occurring at the time of tomosynthesis imaging, the second imaging condition is set. Thus, it is possible to immediately perform simple imaging without performing positioning of the breast M as a subject again. Therefore, according to the second embodiment, it is also possible to reduce a burden on a patient as a subject in a case where body movement occurs.

In the second embodiment, the body movement determination unit 32 detects one correspondence point from the projection images Gi and determines whether or not body movement is occurring, but the present invention is limited to this. The body movement determination unit 32 may detect a plurality of correspondence points from the respective projection images Gi, calculate the magnitude of the deviation between the correspondence point and the projection position with respect to each of the plurality of correspondence points, and determine whether or not body movement is occurring on the basis of the statistical value of the magnitudes of the deviation with respect to the plurality of correspondence points.

In this case, the body movement determination unit 32 determines whether or not body movement is occurring at each of the plurality of correspondence points, on the basis of the magnitude of the deviation at each of the plurality of correspondence points, and calculates a ratio of the number of correspondence points, for which it is determined that body movement is occurring, to the number of the plurality of correspondence points. Then, in a case where the calculated ratio is predetermined and equal to or greater than a predetermined threshold value Th4, the body movement determination unit 32 may determine that body movement is occurring. The threshold value Th4 may be set to 0.5, for example, but the present invention is not limited to this.

As another method of determining whether or not body movement is occurring on the basis of the magnitudes of the deviation of the plurality of correspondence points, the body movement determination unit 32 calculates a statistical value of the calculated statistical values of the deviation as a different statistical value for each of the plurality of correspondence points. Then, in a case where the calculated other statistical value is equal to or greater than the predetermined threshold value Th5, the body movement determination unit 32 may determine that body movement is occurring. As the threshold value Th5, it is possible to use experimentally calculated values that can be regarded as body movement occurring in a case where the statistical value is greater than the threshold value Th5.

In each of the above-mentioned embodiments, the notification unit 34 performs simple imaging by notifying that the simple imaging is to be performed, whereby the operator performs simple imaging, but the present invention is not limited to this. In a case where the body movement determination unit 32 determines that body movement is occurring at the time of tomosynthesis imaging, the image acquisition unit 31 may move the X-ray source 16 to the radiation source position Sc and perform simple imaging.

In the above-mentioned embodiments, the subject is the breast M, but the present invention is not limited to this. It is apparent that an optional unit such as the chest or abdomen of the human body may be set as the subject.

Further, body movement may be determined using a method different from each of the above embodiments. For example, body movement may be determined using a known method described in the specification of U.S. Pat. No. 9,498,180A or the like. The method described in the specification of U.S. Pat. No. 9,498,180A is a method of detecting body movement on the basis of the difference between the position of the actual reference point detected in the projection image and the predicted position of the reference point predicted from the plurality of projection images.

What is claimed is:

1. An imaging control device comprising:
   an image acquisition unit that moves a radiation source relative to a detection unit and that acquires a plurality of projection images, which are generated by causing an imaging apparatus to perform tomosynthesis imaging for irradiating a subject with radiation under a first imaging condition for tomosynthesis imaging and which respectively correspond to a plurality of radiation source positions, at the plurality of radiation source positions obtained by movement of the radiation source;
   a body movement determination unit that determines whether or not body movement of the subject is occurring during the tomosynthesis imaging on the basis of the plurality of projection images; and
   a condition setting unit that sets a second imaging condition for simple imaging in the imaging apparatus in a case where the body movement is occurring.

2. The imaging control device according to claim 1, further comprising a reconstruction unit that reconstructs the plurality of projection images so as to generate a tomographic image on one tomographic plane of the subject,
   wherein the body movement determination unit detects at least one feature point from the tomographic image, calculates projection positions of the at least one feature point in the plurality of projection images, and determines whether or not the body movement is occurring on the basis of at least one of directions of movement or amounts of movement of the projection positions between the plurality of projection images.

3. The imaging control device according to claim 2, wherein the body movement determination unit has a discriminator that learned to determine whether or not body movement is occurring on the basis of at least one of directions of movement or amounts of movement of various projection positions, inputs at least one of the directions of movement or the amounts of movement of the projection positions to the discriminator, and determines whether or not the body movement is occurring on the basis of an output of the discriminator.

4. The imaging control device according to claim 2, wherein the body movement determination unit detects a plurality of feature points from the tomographic image, calculates projection positions in the plurality of projection images for each of the plurality of feature points, determines whether or not the body movement is occurring on the basis of at least one of the directions of movement or the amounts of movement of the projection positions between the plurality of projection images for each of the plurality of feature points, and determines whether or not the body movement is occurring on the basis of a determination result for each of the plurality of feature points.

5. The imaging control device according to claim 3, wherein the body movement determination unit detects a plurality of feature points from the tomographic image, calculates projection positions in the plurality of projection images for each of the plurality of feature points, determines whether or not the body movement is occurring on the basis of at least one of the directions of movement or the amounts of movement of the projection positions between the plurality of projection images for each of the plurality of feature points, and determines whether or not the body movement is occurring on the basis of a determination result for each of the plurality of feature points.

6. The imaging control device according to claim 4, wherein the body movement determination unit determines that the body movement is occurring in a case where a ratio of the number of the feature points, for which it is determined that the body movement is occurring, to the number of the plurality of feature points is equal to or greater than a predetermined threshold value.

7. The imaging control device according to claim 5, wherein the body movement determination unit calculates a statistical value of output values of the discriminator at each of the plurality of feature points, and determines that the body movement is occurring in a case where the statistical value is equal to or greater than a predetermined threshold value.

8. The imaging control device according to claim 1, wherein the body movement determination unit detects at least one correspondence point between the plurality of projection images, reconstructs a correspondence point between the plurality of projection images, specifies at least one position of a structure indicating the correspondence point in the subject, calculates a projection position of the position of the structure in the plurality of projection images, calculates a distance between the correspondence point and the projection position in each of the plurality of projection images, and determines whether or not the body movement is occurring in accordance with whether or not a statistical value of the distances for the plurality of projection positions is equal to or greater than a predetermined threshold value.

9. The imaging control device according to claim 8, wherein the body movement determination unit detects a plurality of correspondence points between the plurality of projection images, specifies each of positions of a plurality of structures indicating the plurality of correspondence points in the subject for each of the plurality of correspondence points, calculates projection positions of the positions of the plurality of structures in the plurality of projection images, calculates each of distances between the correspondence points and the corresponding projection positions in the plurality of projection images for each of the plurality of correspondence points, determines whether or not a statistical value of the distances for the correspondence points is equal to or greater than a predetermined threshold value for each of the plurality of projection images, and determines whether or not the body movement is occurring on the basis of a determination result of each of the plurality of correspondence points.

10. The imaging control device according to claim 9, wherein the body movement determination unit determines that the body movement is occurring in a case where a ratio of the number of the correspondence points, for which it is determined that the body movement is occurring, to the number of the plurality of correspondence points is equal to or greater than a predetermined threshold value.

11. The imaging control device according to claim 9, wherein the body movement determination unit further calculates, as a different statistical value, a statistical value of the statistical values of the distances for each of the plurality of correspondence points and determines that the body movement is occurring in a case where the different statistical value is equal to or greater than a predetermined threshold value.

12. The imaging control device according to claim 1, further comprising a notification unit that notifies that the simple imaging is to be performed in a case where the body movement is occurring.

13. The imaging control device according to claim 1, wherein the image acquisition unit acquires a two-dimensional image of the subject, which is generated by causing the imaging apparatus to perform the simple imaging.

14. The imaging control device according to claim 1, wherein the first imaging condition and the second imaging condition are different in terms of at least one of kinds of a target and a filter of the radiation source, a tube voltage of the radiation source, a dose of radiation from the radiation source, or presence or absence of a scattered radiation removal grid for removing a scattered radiation component included in the radiation transmitted through the subject.

15. The imaging control device according to claim 1, wherein the subject is a breast.

16. An imaging control method comprising:
   moving a radiation source relative to a detection unit and acquiring a plurality of projection images, which are generated by causing an imaging apparatus to perform tomosynthesis imaging for irradiating a subject with radiation under a first imaging condition for tomosynthesis imaging and which respectively correspond to a plurality of radiation source positions, at the plurality of radiation source positions obtained by movement of the radiation source;
   determining whether or not body movement of the subject is occurring during the tomosynthesis imaging on the basis of the plurality of projection images; and
   setting a second imaging condition for simple imaging in the imaging apparatus in a case where the body movement is occurring.

17. A non-transitory computer-readable storage medium that stores an imaging control program causing a computer to execute steps of:
   moving a radiation source relative to a detection unit and acquiring a plurality of projection images, which are generated by causing an imaging apparatus to perform tomosynthesis imaging for irradiating a subject with radiation under a first imaging condition for tomosynthesis imaging and which respectively correspond to a plurality of radiation source positions, at the plurality of radiation source positions obtained by movement of the radiation source;
   determining whether or not body movement of the subject is occurring during the tomosynthesis imaging on the basis of the plurality of projection images; and
   setting a second imaging condition for simple imaging in the imaging apparatus in a case where the body movement is occurring.

* * * * *